US012589198B2

(12) United States Patent
Vale et al.

(10) Patent No.: US 12,589,198 B2
(45) Date of Patent: Mar. 31, 2026

(54) CYCLIC ASPIRATION SYSTEM PRODUCING CYCLIC ASPIRATION PRESSURE WAVEFORM USING VACUUM PUMP AND POSITIVE PRESSURE PULSE GENERATOR MECHANISM

(71) Applicant: Neuravi Limited, Galway (IE)

(72) Inventors: David Vale, Barna (IE); Alan Carney, Galway (IE)

(73) Assignee: NEURAVI LIMITED, Galway (IE)

( * ) Notice: Subject to any disclaimer, the term of this patent is extended or adjusted under 35 U.S.C. 154(b) by 119 days.

(21) Appl. No.: 18/441,374

(22) Filed: Feb. 14, 2024

(65) Prior Publication Data

US 2024/0277355 A1     Aug. 22, 2024

Related U.S. Application Data

(60) Provisional application No. 63/447,506, filed on Feb. 22, 2023.

(51) Int. Cl.
A61M 1/00        (2006.01)
A61B 17/22        (2006.01)
(Continued)

(52) U.S. Cl.
CPC .............. A61M 1/75 (2021.05); A61B 17/22 (2013.01); A61B 17/221 (2013.01); A61M 1/842 (2021.05);
(Continued)

(58) Field of Classification Search
CPC ...... A61M 1/75; A61M 1/842; A61M 25/003; A61M 25/0068; A61M 25/0074;
(Continued)

(56) References Cited

U.S. PATENT DOCUMENTS

2002/0198550 A1    12/2002    Nash et al.
2004/0019310 A1     1/2004    Hogendijk
(Continued)

FOREIGN PATENT DOCUMENTS

WO        WO-2014151209 A1 *    9/2014    .............. A61M 1/75

OTHER PUBLICATIONS

Partial International Search Report issued in International Application No. PCT/IB2024/051648, dated May 28, 2024, and submitted herewith.

*Primary Examiner* — Richard G Louis
(74) *Attorney, Agent, or Firm* — Troutman Pepper Locke LLP

(57)            ABSTRACT

Cyclic aspiration system producing a cyclic aspiration pressure waveform of intermittent cyclic intervals of vacuum pressure below atmospheric pressure and a positive pressure higher than the vacuum pressure. The system including an aspiration catheter, a vacuum pump, and connected in fluid communication therebetween a positive pressure pulse generator mechanism including at least one displaceable member displaceable within a housing, wherein the at least one displaceable member controls passage therethrough the housing of the vacuum pressure and produces the positive pressure pulse by compressing collectable fluid therein. The system further including at least one actuator arranged externally of the housing displacing the at least one displaceable member within the housing.

14 Claims, 13 Drawing Sheets

(51) Int. Cl.

| | |
|---|---|
| *A61B 17/221* | (2006.01) |
| *A61B 17/00* | (2006.01) |
| *A61M 25/00* | (2006.01) |
| *A61M 25/01* | (2006.01) |
| *A61M 25/10* | (2013.01) |

(52) U.S. Cl.
CPC .............. *A61B 2017/00022* (2013.01); *A61B 2017/00154* (2013.01); *A61B 2017/00172* (2013.01); *A61B 2017/0023* (2013.01); *A61B 2017/00292* (2013.01); *A61B 2017/00367* (2013.01); *A61B 2017/00398* (2013.01); *A61B 2017/00544* (2013.01); *A61B 2017/00561* (2013.01); *A61B 2017/00862* (2013.01); *A61B 2017/00867* (2013.01); *A61B 2017/22067* (2013.01); *A61B 2017/22079* (2013.01); *A61B 2017/2212* (2013.01); *A61B 2017/2215* (2013.01); *A61B 2217/005* (2013.01); *A61M 2025/0002* (2013.01); *A61M 2025/0004* (2013.01); *A61M 25/003* (2013.01); *A61M 2025/0031* (2013.01); *A61M 2025/0039* (2013.01); *A61M 2025/0059* (2013.01); *A61M 25/0068* (2013.01); *A61M 25/0074* (2013.01); *A61M 25/0158* (2013.01); *A61M 2025/1052* (2013.01); *A61M 2205/3327* (2013.01); *A61M 2205/3351* (2013.01)

(58) Field of Classification Search
CPC ...... A61M 25/0158; A61M 2025/0002; A61M 2025/0004; A61M 2025/0031; A61M 2025/0039; A61M 2025/0059; A61M 2025/1052; A61M 2205/3327; A61M 2205/3351; A61M 1/67; A61M 1/74; A61M 1/80; A61M 1/81; A61B 17/22; A61B 17/221; A61B 2017/00022; A61B 2017/00154; A61B 2017/00172; A61B 2017/0023; A61B 2017/00292; A61B 2017/00367; A61B 2017/00398; A61B 2017/00544; A61B 2017/00561; A61B 2017/00862; A61B 2017/00867; A61B 2017/22067; A61B 2017/22079; A61B 2017/2212; A61B 2017/2215; A61B 2217/005

See application file for complete search history.

(56) References Cited

U.S. PATENT DOCUMENTS

| | | |
|---|---|---|
| 2011/0034986 A1 | 2/2011 | Chou et al. |
| 2016/0135829 A1 | 5/2016 | Holochwost et al. |
| 2019/0239910 A1 | 8/2019 | Brady et al. |
| 2020/0129751 A1 | 4/2020 | Malkowski et al. |

\* cited by examiner

CYCLIC ASPIRATION SYSTEM PRODUCING CYCLIC ASPIRATION PRESSURE WAVEFORM USING VACUUM PUMP AND POSITIVE PRESSURE PULSE GENERATOR MECHANISM

CROSS-REFERENCE TO RELATED APPLICATION

This application claims the benefit of U.S. Provisional Patent Application No. 63/447,506 filed on Feb. 22, 2023, the disclosure of which is incorporated herein by reference in its entirety.

FIELD

The present disclosure generally relates to a system and method used during thrombectomy procedures for the capture and removal of occlusions or clots. Specifically, the present disclosure relates to a cyclic aspiration system for the capture and removal of occlusions or clots in a vessel where the cyclic aspiration pressure waveform includes intermittent cyclic intervals of vacuum pressure (i.e., below atmospheric pressure) and positive pressure (i.e., higher than vacuum pressure, possibly higher than atmospheric pressure). The cyclic aspiration system produces the cyclic aspiration waveform using a positive pressure pulse generator mechanism associated with a housing disposed in fluid communication between a vacuum pump and aspiration catheter, wherein the positive pressure pulse generator mechanism using at least one displaceable member displaceable within the housing via at least one actuator arranged externally thereof controls (i.e., allowing or prohibiting) passage of the vacuum pressure therethrough and creates the positive pressure pulse by compressing fluid collectable therein.

BACKGROUND

Pulsatile or cyclic aspiration applies a cyclic pressure waveform of intermittent cyclic minimum/low/vacuum/aspiration pressure and maximum/peak/high pressure. During cycles under the minimum/low/vacuum/aspiration pressure the clot is drawn in the proximal direction and captured at the distal tip/end of the aspiration catheter, whereas during cycles of maximum/peak/high pressure the clot is pushed in the distal direction. When utilizing pulsatile or cyclic aspiration during the capture and removal of the clot it is desirable to maximize the cycling frequency of the cyclic pressure waveform and thus maximize clot vibration thereby optimizing aspiration performance. One key challenge in maximizing the cycling frequency is a particular response time required for mechanical actuation of each active component limiting an extent to which the cycling frequency may be increased. Complex conventional systems for maximizing cycling frequency have many active components each required to await their response times before being activated to maintain normal operation. Accordingly, in complex systems with many active components the extent to which the cycling frequency may be maximized is undesirably curtailed. Another concern is that conventional aspiration systems are prone to clogging by the captured clot.

It is therefore desirable to develop an improved cyclic aspiration system utilizing as few active components as possible with an associated maximized response time to attain maximum cycling frequency while also minimizing dampening or decay of the positive pressure wave as well as the additional benefit of reducing the overall cost of manufacture. Still further desirable is to develop an improved cyclic aspiration system preventing, or minimizing, risk of clogging.

SUMMARY

An aspect of the present disclosure relates to a pulsatile or cyclic aspiration system producing a cyclic aspiration pressure waveform of intermittent cyclic intervals of vacuum pressure below atmospheric pressure and positive pressure higher than vacuum pressure (higher than vacuum pressure, possibly higher than atmospheric pressure) using as few active components as possible with an associated maximized response time to attain maximum cycling frequency while also minimizing dampening or decay of the positive pressure wave as well as the additional benefit of reducing the overall cost of manufacture.

Another aspect of the present disclosure is directed a cyclic aspiration system producing a cyclic aspiration pressure waveform of vacuum pressure below atmospheric pressure and positive pressure higher than vacuum pressure (possibly higher than atmospheric pressure) using a positive pressure pulse generator mechanism disposed in fluid communication between a vacuum pump and aspiration catheter, wherein the positive pressure pulse generator mechanism includes at least one displaceable member displaceable within a housing via an actuator arranged externally thereof controlling (i.e., allowing or prohibiting) passage of the vacuum pressure therethrough and creating the positive pressure pulse by compressing fluid collectable therein.

While still another aspect of the present disclosure is directed to a cyclic aspiration system producing a cyclic aspiration pressure waveform of vacuum pressure below atmospheric pressure and positive pressure higher than vacuum pressure (possibly higher than atmospheric pressure) using a positive pressure pulse generator mechanism including at least one displaceable member displaceable within a housing via at least one actuator arranged externally thereof, wherein to minimize the risk of clogging by the clot the housing and at least one displaceable member are discardable after a single use, while the at least one actuator arranged externally of housing is not contaminated by blood and reusable.

BRIEF DESCRIPTION OF THE DRAWINGS

The above and further aspects of the present disclosure are further discussed with reference to the following description in conjunction with the accompanying drawings, in which like numerals indicate like structural elements and features in various figures. The drawings are not necessarily to scale, emphasis instead being placed upon illustrating principles of the present disclosure. The figures depict one or more implementations of the devices, by way of example only, not by way of limitation.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

As used herein, the terms "tubular" and "tube" are to be construed broadly and are not limited to a structure that is a right cylinder or strictly circumferential in cross-section or of a uniform cross-section throughout its length. For example, a tubular structure or system is generally illustrated as a substantially right cylindrical structure. However, the tubular system may have a tapered or curved outer surface without departing from the scope of the present disclosure.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

Various exemplary cyclic aspiration systems are disclosed herein producing the cyclic aspiration pressure waveform of intermittent cyclic intervals of vacuum pressure (i.e., pressure below atmospheric pressure) and positive pressure (i.e., pressure higher than vacuum pressure, possibly higher than atmospheric pressure) used to capture and remove a clot. Specifically, the present disclosure is directed to a non-vented cyclic aspiration systems, i.e., a cyclic aspiration system that is not vented to any of the following: (i) atmospheric pressure, (ii) a liquid reservoir open to atmospheric pressure, or a (iii) pressurized closed reservoir (herein referred to as a non-vented cyclic aspiration system). Instead, the cyclic aspiration pressure waveform is produced in accordance with the present disclosure using only a vacuum pump and a positive pressure pulse generator mechanism disposed between the vacuum pump and the aspiration catheter. The positive pressure pulse generator mechanism includes at least one displaceable member that when displaced within a housing controls passage therethrough of the vacuum pressure generated by the vacuum pump and also generates a positive pressure pulse.

Figures 1A, 1B, 1C:
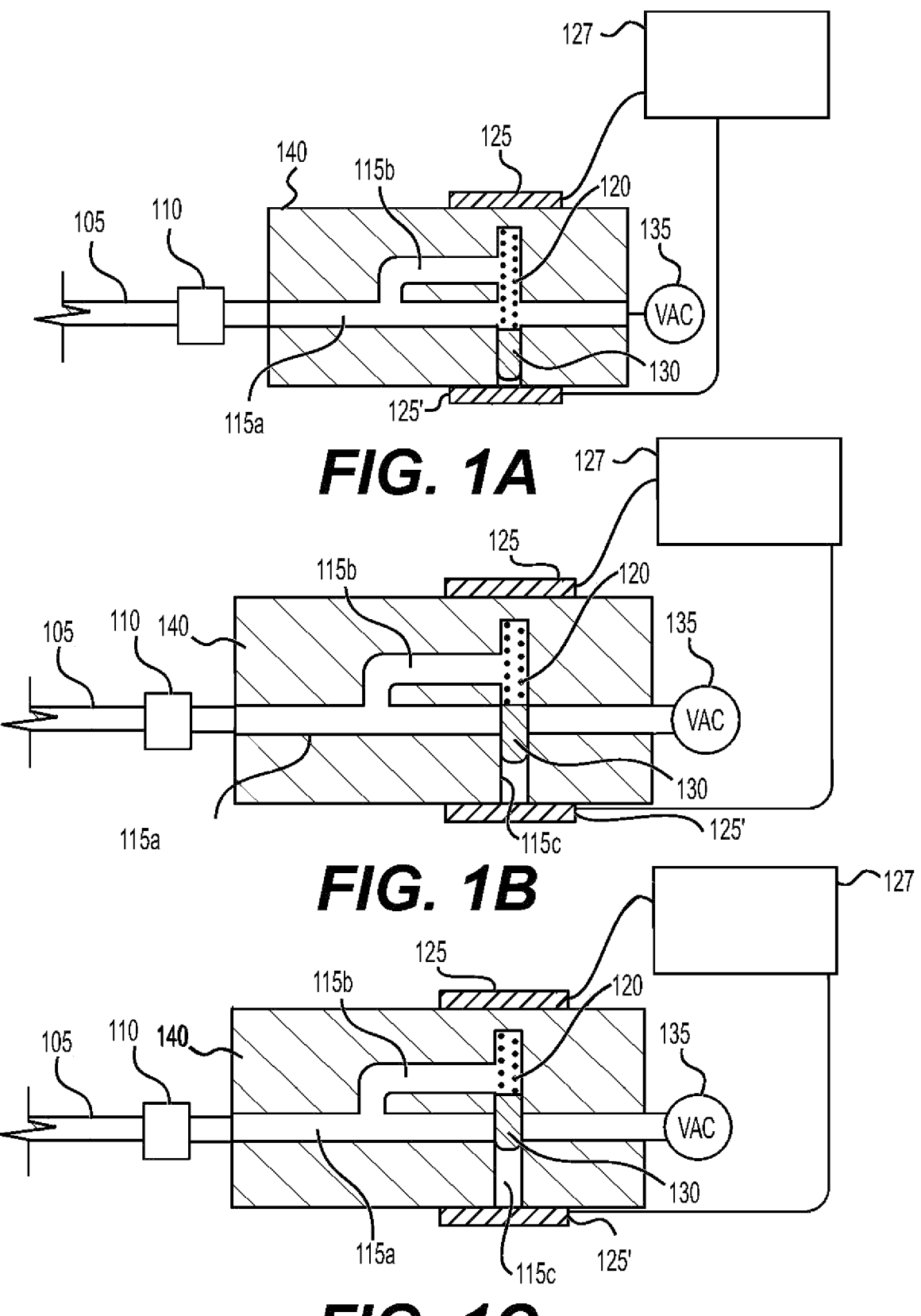
FIG. 1A is an example cyclic aspiration system in accordance with the present disclosure producing the cyclic aspiration pressure waveform using a vacuum pump and a single electrically conductive plunger slidable within an auxiliary channel defined in a housing in response to two electromagnets arranged externally of the housing; depicting the single electrically conductive plunger positioned in the auxiliary channel allowing unrestricted passage through the vacuum pressure channel (i.e., open state) of the vacuum pressure generated by the vacuum pump.
FIG. 1B is the example cyclic aspiration system of FIG. 1A depicting the single electrically conductive plunger positioned within the auxiliary channel blocking or preventing passage through the vacuum pressure channel (i.e., closed state) of the vacuum pressure generated by the vacuum pump.
FIG. 1C is the example cyclic aspiration system of FIG. 1A depicting the single electrically conductive plunger further advanced in position in the auxiliary channel compressing an internal spring while displacing the fluid collectable in the system thereby generating the positive pressure pulse in the positive pressure pulse channel while the vacuum pressure channel remains blocked (i.e., closed state) preventing passage of the vacuum pressure therethrough.

An exemplary cyclic aspiration system in accordance with the present disclosure is shown in FIGS. 1A-1C in which the positive pressure pulse generator is a single displaceable plunger that serves to both control passage therethrough of the vacuum pressure generated by the vacuum pump and generate the positive pressure pulse. FIG. 1A-1C depict a module, unit, or housing 140 (preferably plastic molded) disposed between a vacuum pump 135 and a proximal hub 110 attached to the aspiration catheter 105. The housing 140 has defined therein a vacuum pressure channel 115a connected in fluid communication between the vacuum pump 130 and the aspiration catheter 105, a positive pressure channel 115b, and an auxiliary channel 115c. All three channels 115a, 115b, 115c being in fluid communication with one another. A single electrically conductive plunger 130 is slidable or displaceable against a spring 120 within the auxiliary channel 115c by energizing/de-energizing two electromagnets (e.g., first electromagnet 125 and second electromagnet 125') disposed externally of the housing 140 at opposite ends of the auxiliary channel 115c. The plunger 130 may incorporate a seal or one or more seals may be configured within the auxiliary channel 115c of the housing 140 itself. Alternatively, the plunger 130 may be tightly fit within the auxiliary channel 115c of the housing 140 so that a separate seal is not required. To generate an interval of vacuum pressure, the first electromagnet 125 is de-energized while the second electromagnet 125' is energized (e.g., power source 127 or battery) drawing the plunger 130 thereto so that the vacuum pressure channel 115a is in an open state allowing unrestricted passage therethrough of the vacuum pressure generated by the vacuum pump 135 (FIG. 1A). Thereafter, generation of the positive pressure pulse is a two-stage process. During an initial or preliminary stage depicted in FIG. 1B, the second electromagnet 125' is de-energized, while the first electromagnet 125 is energized to a preliminary (i.e., initial) level advancing the plunger 130 within the auxiliary channel 115c to a position occluding (i.e., closing off) the vacuum pressure channel 115a prohibiting passage therethrough of the vacuum pressure generated by the vacuum pump 135. Thereafter, with the application of additional energy to the first electromagnet 125 the plunger 130 is drawn further thereto displacing (i.e., compressing) the fluid (e.g., blood and/or saline) collected therein thereby creating a positive pressure pulse that enters the positive pressure channel 115b (FIG. 1C). In the example shown, spring 120 (or other restorative member) is disposed within the auxiliary channel 115c to limit displacement of the plunger 130 and/or assist in its return back towards its position shown in FIG. 1A. Instead of or in addition to spring 120, it is also contemplated to include within the auxiliary channel 115c a repositionable limit stop to alter the maximum stroke length of the plunger 130 and hence vary the magnitude (i.e., amplitude or pressure level) of the resultant generated pressure pulse, as described in further detail below regarding the example in FIGS. 2A & 2B. The pressure level of the generated positive pressure pulse is directly proportional to the displacement (i.e., maximum stroke length) of the plunger 130 within the auxiliary channel 115c of the housing 140, which may be controlled by the position of the electromagnets and/or the energy applied to them.

Figures 1D, 1E, 1F:
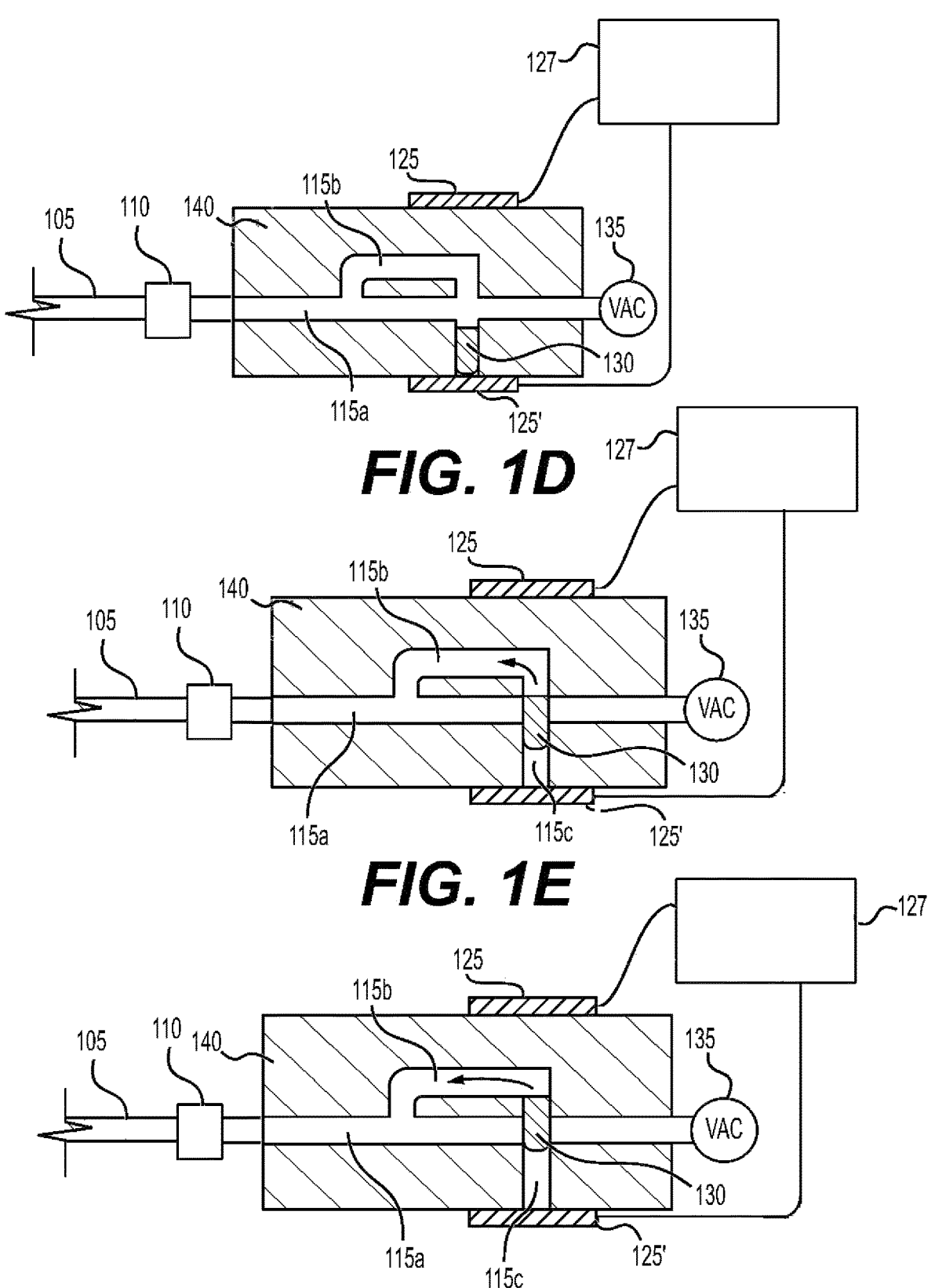
FIG. 1D is another example cyclic aspiration system in accordance with the present disclosure producing the cyclic aspiration pressure waveform using a vacuum pump and a single electrically conductive plunger slidable within an auxiliary channel defined in a housing in response to two electromagnets arranged externally of the housing; depicting the single electrically conductive plunger positioned in the auxiliary channel allowing unrestricted maximum passage through vacuum pressure channel (i.e., open state) of the vacuum pressure generated by the vacuum pump.
FIG. 1E is the example cyclic aspiration system of FIG. 1D depicting the single electrically conductive plunger positioned within the auxiliary channel blocking or preventing passage through the vacuum pressure channel (i.e., closed state) of the vacuum pressure generated by the vacuum pump.
FIG. 1F is the example cyclic aspiration system of FIG. 1D depicting the single electrically conductive plunger further advanced in position in the auxiliary channel displacing (e.g., compressing) the fluid collectable in the system thereby generating the positive pressure pulse in the positive pressure channel while the vacuum pressure channel remains blocked (i.e., closed state) preventing passage of the vacuum pressure therethrough.

FIGS. 1D-1F represent an exemplary modified arrangement of the configuration of the auxiliary channel 115c defined in the housing 140 in FIGS. 1A-1C. In FIGS. 1D-1F the positive pressure channel 115b is connected in fluid communication at both ends with the vacuum pressure channel 115a, thereby eliminating the need for the spring 120 since regardless of the displacement of the plunger 130 within the auxiliary channel 115c the positive pressure channel 115b will never be blocked or occluded. In all other respects operation is the same as that of described with respect to the example in FIG. 1A-1C. The more energy imparted to the first electromagnet 125 the further advancement or travel of the plunger 130 within the auxiliary channel 115c producing a greater magnitude positive pressure pulse. As the plunger 130 travels (FIG. 1F), the pressure within the system approaches zero and can overshoot into pressure above zero depending on its travel distance within the auxiliary channel 115c.

Figure 2A:
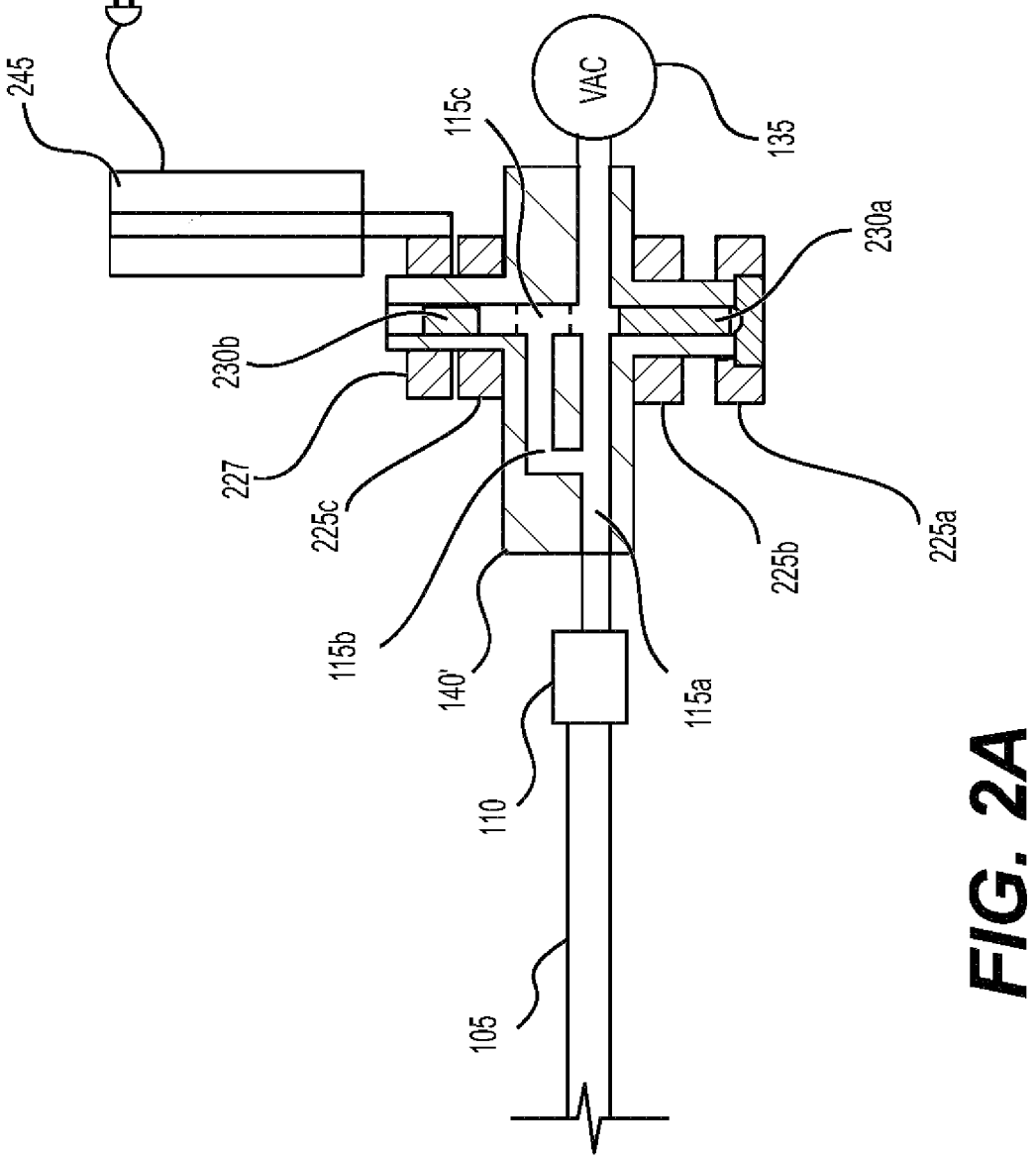
FIG. 2A is yet another example cyclic aspiration system in accordance with the present disclosure producing the cyclic aspiration pressure waveform using a vacuum pump and two electrically conductive plungers (e.g., a vacuum pressure plunger and a positive pressure plunger) slidable within an auxiliary channel defined in a housing in response to four electromagnets (one of which is adjustable in position) arranged externally of the housing; depicting the vacuum pressure plunger positioned in the auxiliary channel allowing unrestricted passage through the vacuum pressure channel (i.e., open state) of the vacuum pressure generated by the vacuum pump.
Figure 2C:
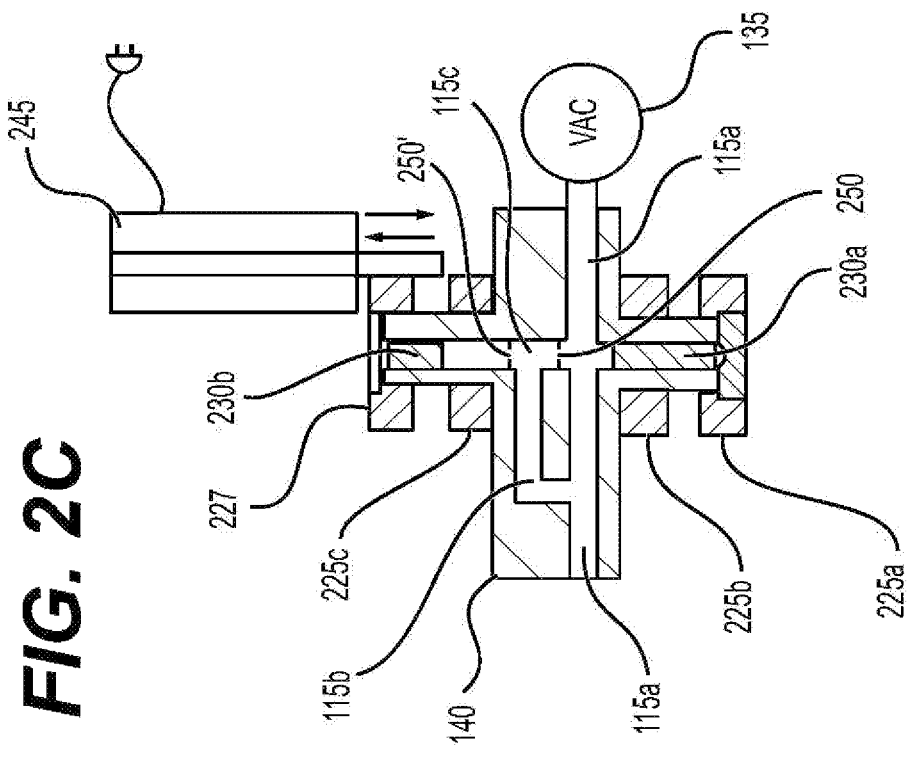
FIG. 2C is the example cyclic aspiration system of FIG. 2A illustrating varying the amplitude of the generated positive pressure pulse by repositioning the one adjustable electromagnet using a linear actuator to change the stroke length of the positive pressure plunger.
Figure 2B:
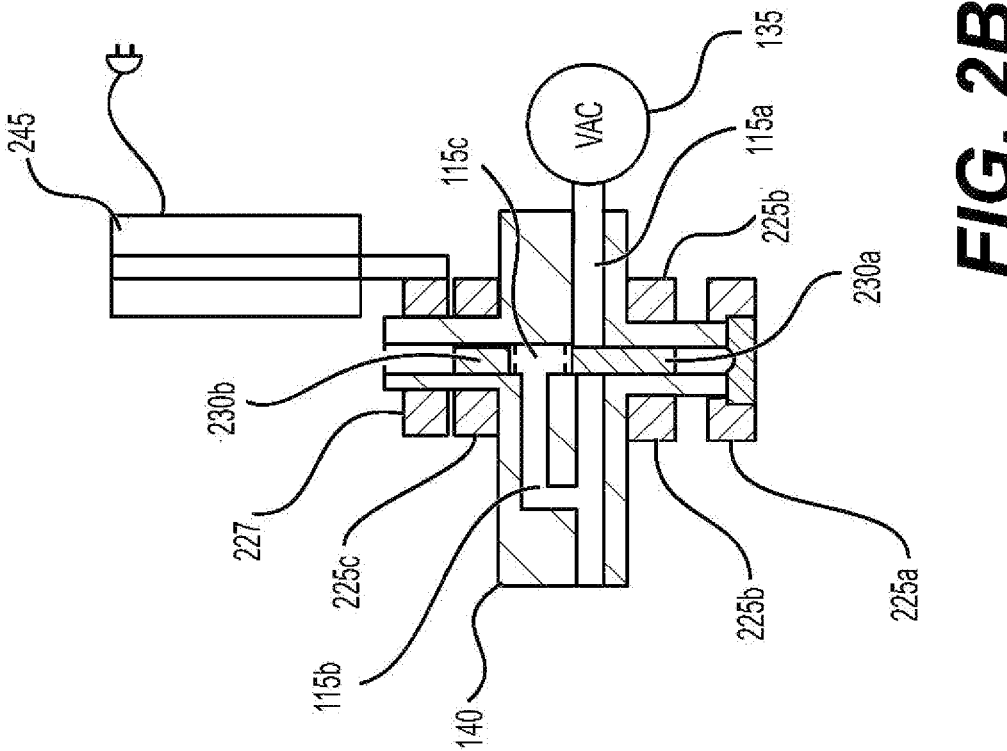
FIG. 2B is the example cyclic aspiration system of FIG. 2A depicting the positive pressure plunger advanced in position in the auxiliary channel displacing (e.g., compressing) the fluid collectable in the system thereby generating the positive pressure pulse in the positive pressure channel while the vacuum pressure channel remains blocked (i.e., closed state) by the vacuum pressure plunger preventing passage of the vacuum pressure therethrough.

FIGS. 2A-2C depict another exemplary non-vented cyclic aspiration system in accordance with the present disclosure. This system is similar to that described in FIGS. 1A-1C above except that that the two actions of opening/closing the vacuum pressure channel to control passage of the vacuum pressure therethrough and creating the positive pressure pulse are now performed by two separate plungers, each independently actuated using a separate associated set of electromagnetic actuators. The housing 240 (e.g., molded plastic) in FIGS. 2A-2C has defined therein a vacuum pressure channel 115a connected in fluid communication between the vacuum pump 135 and the aspiration catheter 105, a positive pressure channel 115b, and an auxiliary channel 115c. All three channels 115a, 115b, 115c being connected in fluid communication. Two electrically conductive plungers (e.g., made of a conductive metal or having a conductive metal feature) are independently displaceable of one another within the auxiliary channel 115c. Specifically, a vacuum pressure plunger 230a acts as a valve (i.e., open/close) the vacuum pressure channel 115a to control passage therethrough of the vacuum pressure generated by the vacuum pump, while a positive pressure plunger 230b compresses fluid collected in the system thereby generating the positive pressure pulse. Displacement of the two plungers 230a, 230b is realized by energizing/de-energizing three stationary (i.e., fixed in position) electromagnets (e.g., first electromagnet 225a, second electromagnet 225b, third electromagnet 225c) and a fourth adjustable in position electromagnet 227 all disposed externally of the housing 240 arranged in an axial direction along the auxiliary channel 115c. Specifically, with respect to the vacuum pressure channel 115a and the positive pressure channel 115b arranged in the center, the first and second electromagnets 225a, 225b are disposed to one side while the third and fourth electromagnets 225c, 227 are disposed to the opposite side. To generate an interval of vacuum pressure, while the second and third electromagnets 225b, 225c are de-energized, the first and fourth electromagnets 225a, 227 are energized, drawing the vacuum pressure plunger 230a to the first electromagnet 225a depicting the vacuum pressure channel 115a in an open state allowing unrestricted passage therethrough of the vacuum pressure generated by the vacuum pump 135, while the positive pressure plunger 230b is drawn to the fourth electromagnet 227 (i.e., return stroke position of the positive pressure plunger 230b)(FIG. 2A). Thereafter, to generate the positive pressure pulse, while the first and fourth electromagnets 225a, 227 are de-energized the second and third electromagnets 225b, 225c are energized. As a result, the vacuum pressure plunger 230a is drawn to the energized second electromagnet 225b thereby occluding (i.e., closing off) the vacuum pressure channel 115a preventing passage therethrough of the vacuum pressure generated by the vacuum pump, and simultaneously therewith the positive pressure plunger 230b is drawn to the energized third electromagnet 225c compressing the fluid collected therein producing the positive pressure pulse that enters the positive pressure channel 115b (FIG. 2B). The intermittent cycling of the vacuum pressure and positive pressure intervals in FIGS. 2A & 2B, respectively, is continuously repeated to produce the cyclic aspiration pressure waveform. In response to pressure detected by a sensor, the example cyclic aspiration system in FIGS. 2A-2C has the additional capability to control or adjust the amplitude (i.e., pressure level) of the generated positive pressure pulse at any time during the generation of the cyclic aspiration pressure waveform. A linear actuator 245 or other linear displacement mechanism may be used to vary the position of the fourth electromagnet 227 (as indicated by the bi-directional arrows in FIG. 2C) and as a result the return travel or stroke length or of the positive pressure plunger 230b within the auxiliary channel 115c thereby adjusting or controlling the volume of collected fluid being compressed and hence amplitude of the generated positive pressure pulse. Increasing the return stroke length (i.e., fourth electromagnet 227 further away relative to the third electromagnet 225c) increases the amplitude of the generated positive pressure pulse, whereas decreasing the return stroke length (i.e., fourth electromagnet 227 closer towards the third electromagnet 225) decreases the amplitude of the generated positive pressure pulse. In the example shown, stop limits 250, 250' are disposed within the interface tubing 115c to prevent the plungers 230a, 230b, respectively, from occluding or blocking the positive pressure channel 115b. Once again, electromagnets 225a, 225b, 225c, 227 arranged externally of the module or housing 140 remain uncontaminated by blood and thus are reusable, while those inexpensive components (e.g., housing 140 and plungers 230a, 230b) contaminated by blood are discardable after a single use as a single unit.

Figure 3A:
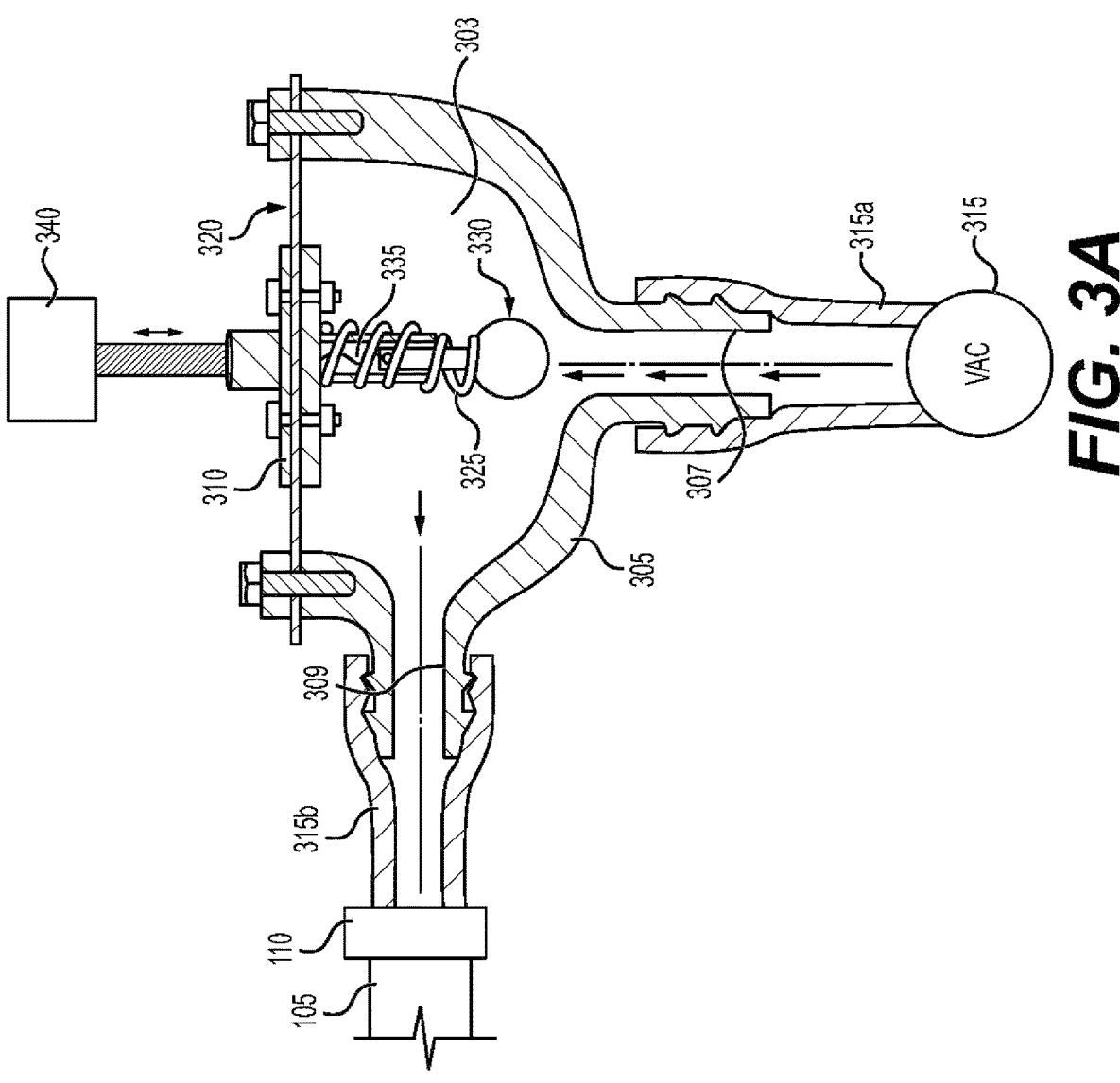
FIG. 3A is still yet another example cyclic aspiration system in accordance with the present disclosure producing the cyclic aspiration pressure waveform using a flexible diaphragm and ball valve securable thereto projecting within a housing (e.g., elbow connector) disposed between the vacuum pump and aspiration catheter; depicting in a default, natural, state the flexible diaphragm and associated ball valve in a retracted position unseated from the vacuum inlet port of the housing allowing unrestricted passage therethrough of the vacuum pressure generated by the vacuum pump.
Figure 3B:
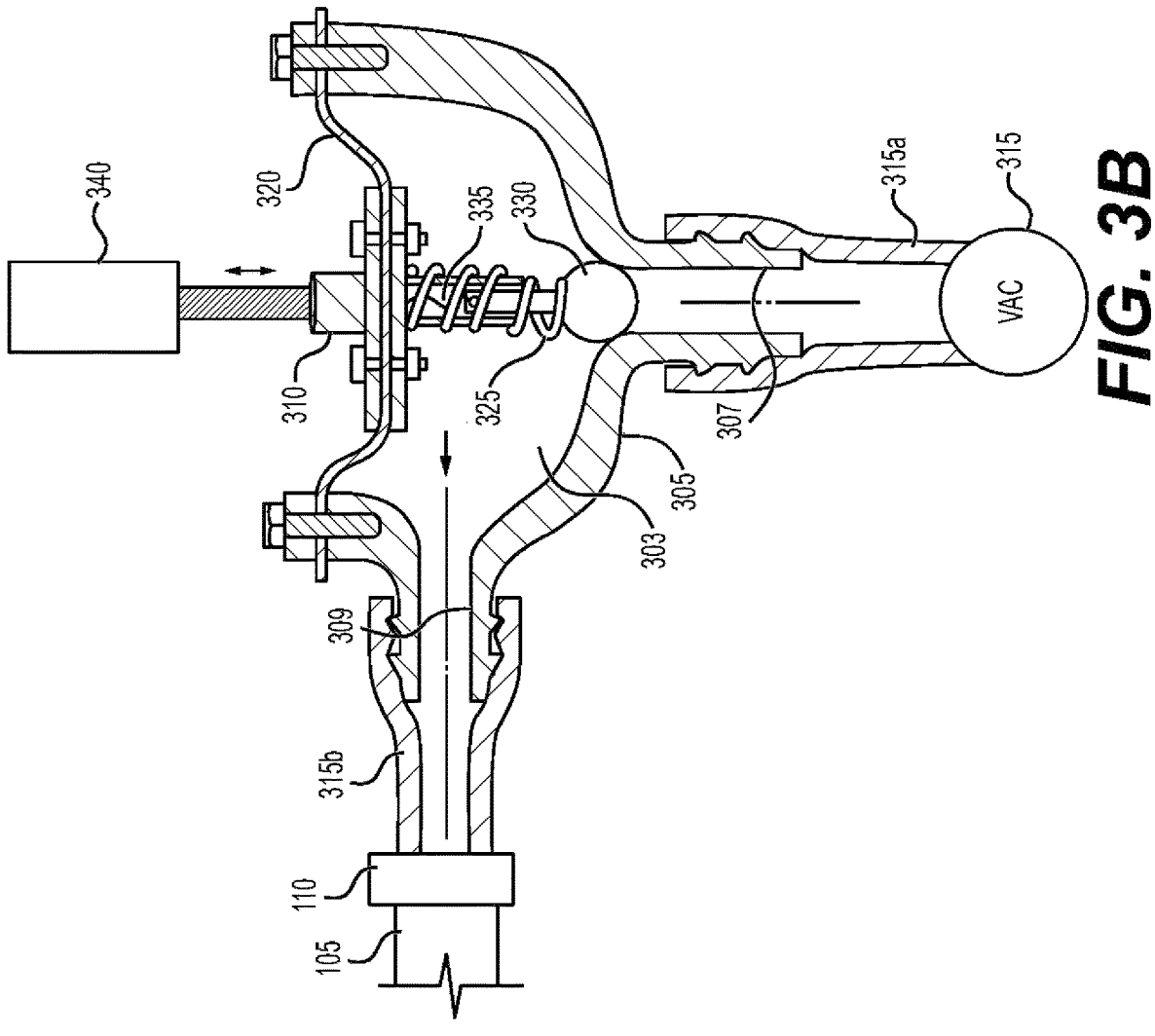
FIG. 3B is the example cyclic aspiration system of FIG. 3A depicting the flexible diaphragm subject to an external axial force via a linear actuator compressing the collectable fluid in the housing generating the positive pressure pulse while simultaneously advancing the ball valve until seated in the vacuum inlet port of the housing preventing passage therethrough of the vacuum pressure generated by the vacuum pump.

FIGS. 3A-3C is yet another example of the positive pressure pulse generator mechanism in accordance with the present disclosure. In this example, the two actions of controlling (e.g., allowing/prohibiting) passage of the vacuum pressure in the vacuum line and creating the positive pressure pulse are performed by two separate components actuated simultaneously using a single actuator. That is, a ball valve 325 serves as a valve (i.e., open/close) allowing or prohibiting passage therethrough of the vacuum pressure while the positive pressure pulse is generated by a flexible diaphragm or membrane 320. By way of example, the flexible diaphragm or membrane 320 in FIGS. 3A & 3B is tautly secured via a releasable securement mechanism (e.g., screws/nuts, clips, or clamps) across an open portion of a rigid housing 305 (e.g., elbow connector). The flexible diaphragm or member 320 is sandwiched between upper and lower rigid support plates 310 (i.e., two separate plates or one plate folded over onto itself) secured together via a releasable mechanical securement mechanism (e.g., screws/nuts, clips, or clamps). Ball valve 325 is mounted to an internal surface of the support plate 310 projecting into an internal cavity 303 of the rigid housing (e.g., elbow connector) 305 having a vacuum pressure inlet port 307 and a positive pressure outlet port 309. The vacuum pressure inlet port 307 of the rigid housing (e.g., elbow connector) 305 is connected in fluid communication either directly or indirectly via vacuum inlet tubing 315a to the vacuum pump 135, while the positive pressure outlet port 309 is connected in fluid communication either directly or indirectly via positive pressure inlet tubing 315b to the proximal hub 110 of the aspiration catheter 105. To generate the cyclic aspiration pressure waveform an external linear actuator 340 (e.g., solenoid or other mechanical displacement mechanism) attached to the support plate(s) 310 cycles between a non-deployed state (i.e., free from application of an axial compressive force) and a deployed state (i.e., imposing an axial compressive force) on the diaphragm or membrane 320 in a direction towards the vacuum pressure inlet port 307. While the linear actuator 340 is in the non-deployed state the flexible diaphragm or membrane 320 is in a default or natural state (i.e., free from axial compression by the linear actuator 340), the ball valve 325 is retracted unseated (i.e., open state) from the vacuum pressure inlet port 307 allowing unrestricted passage therethrough of the vacuum pressure generated by the vacuum pump 135 (FIG. 3A). Whereas, when the linear actuator 340 is in the deployed state imposing an axial compressive force on the diaphragm or membrane 320 the fluid collected in the internal cavity 303 of the housing 305 is also compressed thereby creating the positive pressure pulse that passes through the positive pressure outlet port 309, while simultaneously therewith the ball valve 325 is advanced seated in (i.e., closing off) the vacuum pressure inlet port 307 preventing passage therethrough of the vacuum pressure (FIG. 3B). The connection of the ball valve 325 to the support plate(s) 310 is preferably spring loaded 335 to maximize the allowable axial displacement (i.e., compression) of the diaphragm or membrane 320 to achieve a desired amplitude (i.e., pressure level) of the generated positive pressure pulse tailored on such factors as the fluid injection volume and the aspiration catheter being used.

Figure 4A:
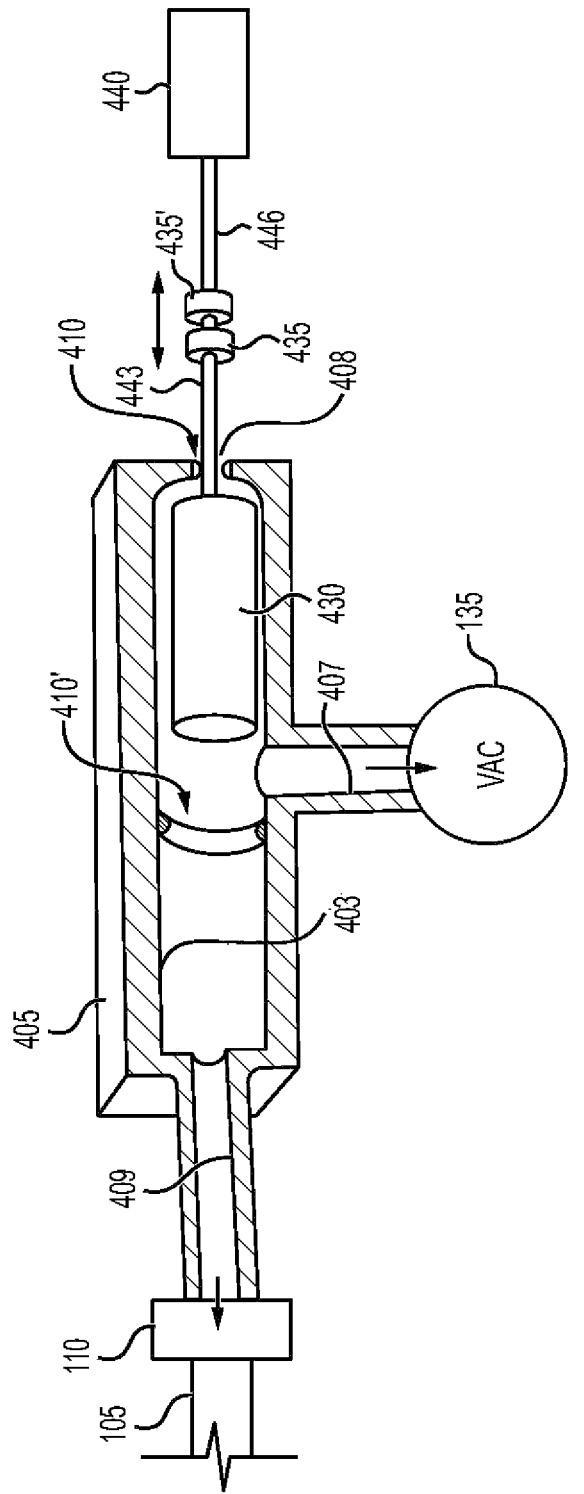
FIG. 4A is another example cyclic aspiration system in accordance with the present disclosure producing the cyclic aspiration pressure waveform using a vacuum pump and a single plunger slidable within a main inner barrel of a rigid housing (e.g., 3-way connector) via an external linear actuator; depicting the single plunger in a retracted state allowing unrestricted passage through a side vacuum pressure inlet port and into the main inner barrel of the rigid housing of the vacuum pressure generated by the vacuum pump.
Figure 4B:
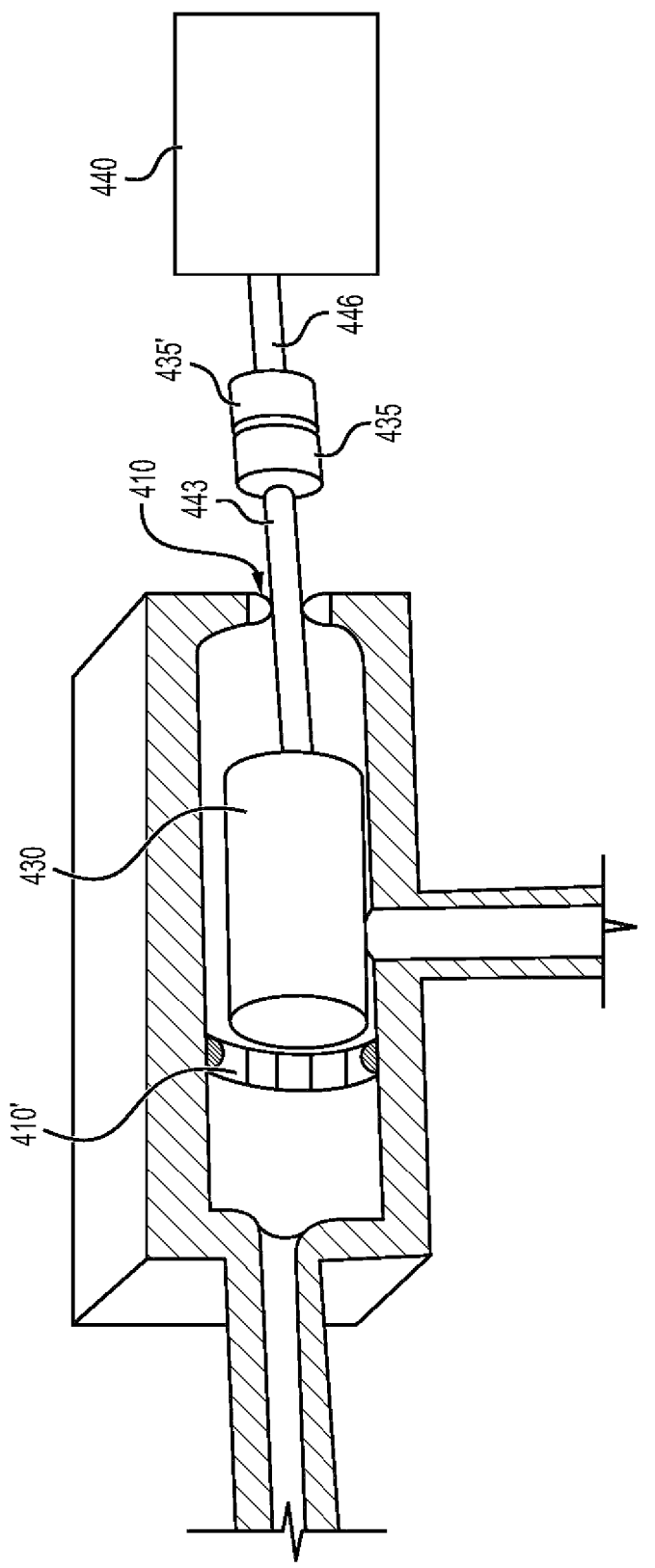
FIG. 4B is the example cyclic aspiration system of FIG. 4A depicting the single plunger advanced in the main inner barrel of the rigid housing displacing (i.e., compressing) the fluid collectable therein thereby generating the positive pressure pulse while simultaneously blocking (i.e., closed state) the side vacuum pressure inlet port preventing passage into the main inner barrel of the vacuum pressure generated by the vacuum pump.

While in still another example in FIGS. 4A & 4B, the positive pressure pulse generator is a single reciprocating plunger 430 slidable within a main inner barrel 403 defined in a rigid housing 405. In this embodiment the single plunger functions both as a valve (e.g., open/close) allowing or blocking passage therethrough of the vacuum pressure and also compressing the fluid collected therein to create the positive pressure pulse. Rigid housing 405 (e.g., 3-way or T-shape connector) includes a proximal port 408 and a distal port 409 with the main inner barrel 403 defined therebetween, while a side port 407 is in fluid communication with the main inner barrel 403. The distal port 409 is connected in fluid communication either directly or indirectly via inlet tubing to the proximal hub 110 of the aspiration catheter 105, while the side port 407 is connected in fluid communication either directly or indirectly via vacuum pressure inlet tubing to the vacuum pump 135. Disposed within the proximal port 408 of the rigid housing 405 is a shaft 443 of the plunger 430 displaceable in the axial direction within the main inner barrel 403 via an external linear displacement mechanism 440 (e.g., driver, linear actuator, solenoid, cam, screw thread, electromagnets, etc.). Complementary coupling or connection fittings 435, 435' (e.g., quick connect such as magnets) may be used to quickly attach the shaft 443 of the single plunger 430 to the shaft 446 of the actuator 440. Preferably, a first seal 410 is provided within the proximal inlet port 408 to prevent leakage of collected fluid and/or cyclic pressure around the shaft 443 of the plunger 430 displaceable therethrough, while a second seal 410' is disposed along an internal wall of the main inner barrel 403 of the rigid housing 405 against which the plunger 430 rests when displaced to ensure complete closing off or blockage of the vacuum pressure through the side port 407. To generate the vacuum pressure interval, the plunger 430 is retracted within the main inner barrel 403 of the rigid housing 405 allowing unrestricted passage through the side port 407 of the vacuum pressure generated by the vacuum pump 135 (FIG. 4A). During a positive pressure cycle, the linear actuator 440 advances the plunger 430 within the main inner barrel 403 of the rigid housing 405 to a position blocking passage of the vacuum pressure through the side port 407 as well as engaging with the second seal 410', while simultaneously compressing the fluid collected in the main inner barrel 403 thereby producing the positive pressure pulse that passes through the distal port 409 (FIG. 4B). The rigid housing 405 in FIGS. 4A & 4B is preferably a single injection molded unit or module. However, it is also contemplated that the rigid housing 405 may be manufactured as a plurality of separate injection molded interlocking components assemblable together. In the example in FIG. 4C, the rigid housing 405 includes 3 separate injection molded interlocking components or parts 405a, 405b, 405c assembled together, however, the rigid housing may be manufactured using any number of two or more separate interlocking components or parts assemblable together.

Figure 4C:
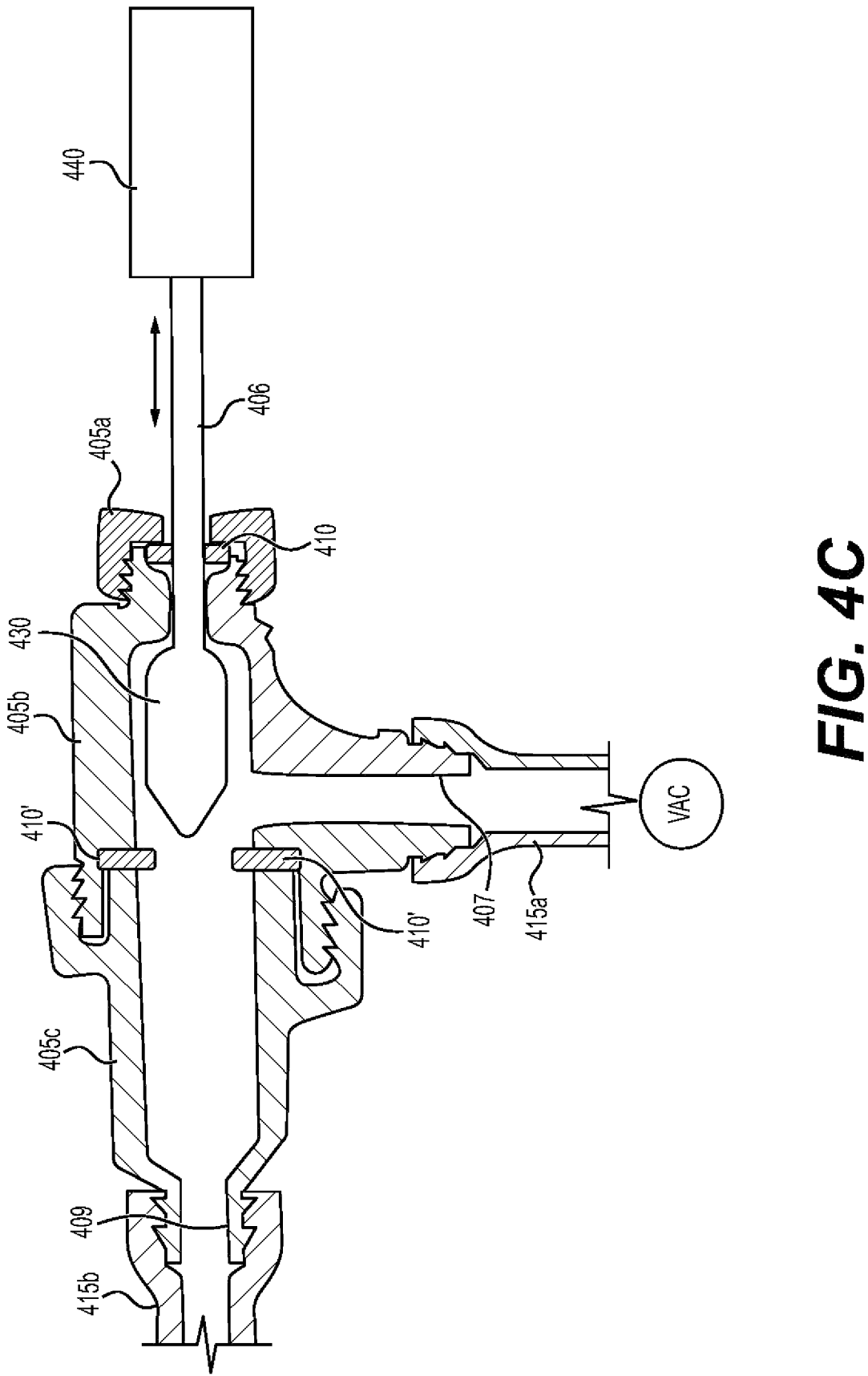
FIG. 4C is an exemplary illustration of the rigid housing (e.g., 3-way connector) of the cyclic aspiration system of FIG. 4A manufactured as three separate interlocking components assembled together.
Figure 5A:
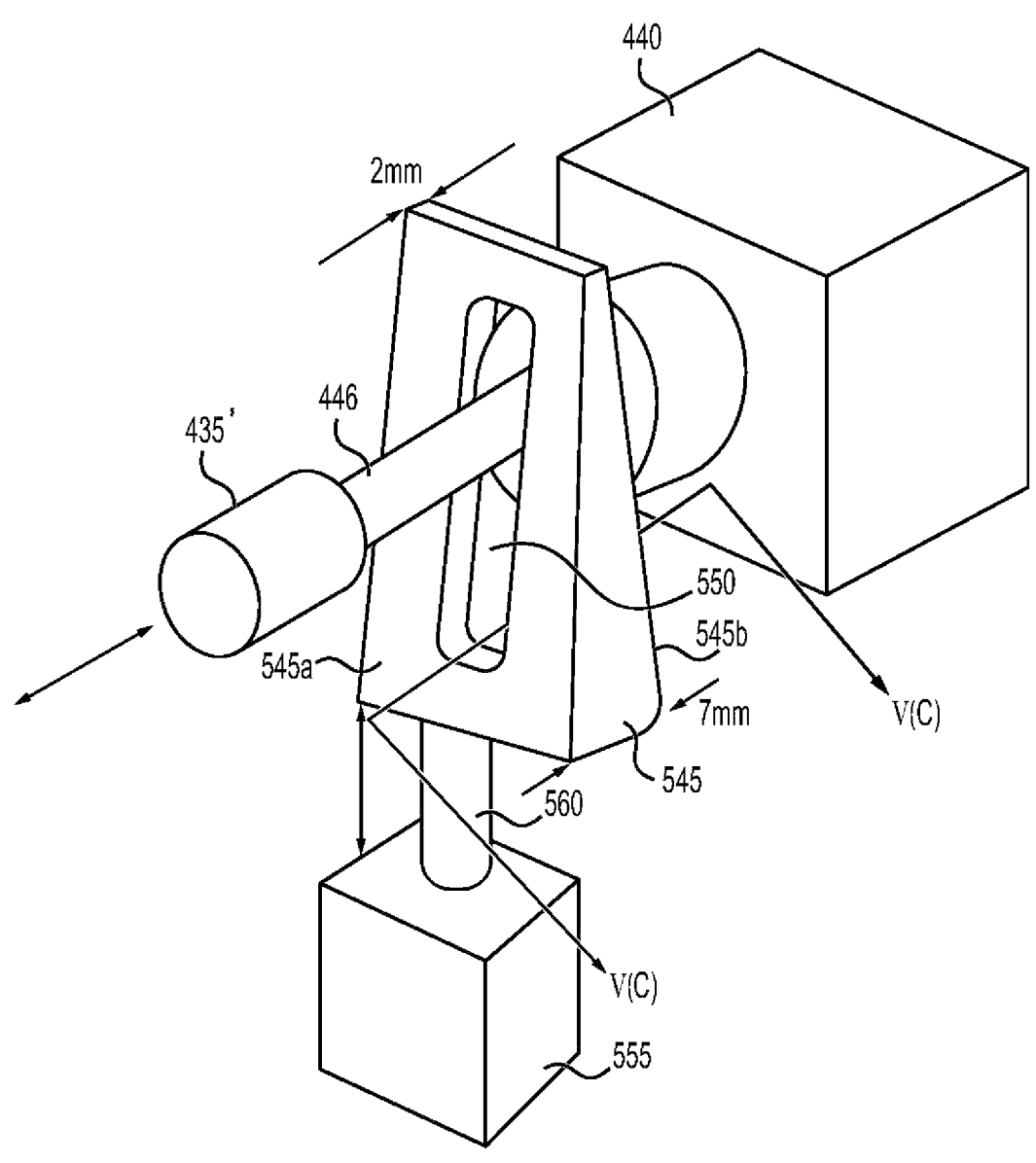
FIG. 5A is a perspective view of an exemplary positive pressure pulse amplitude adjustment mechanism including a tapered shim to vary a maximum displacement by the actuator.
Figure 5B:
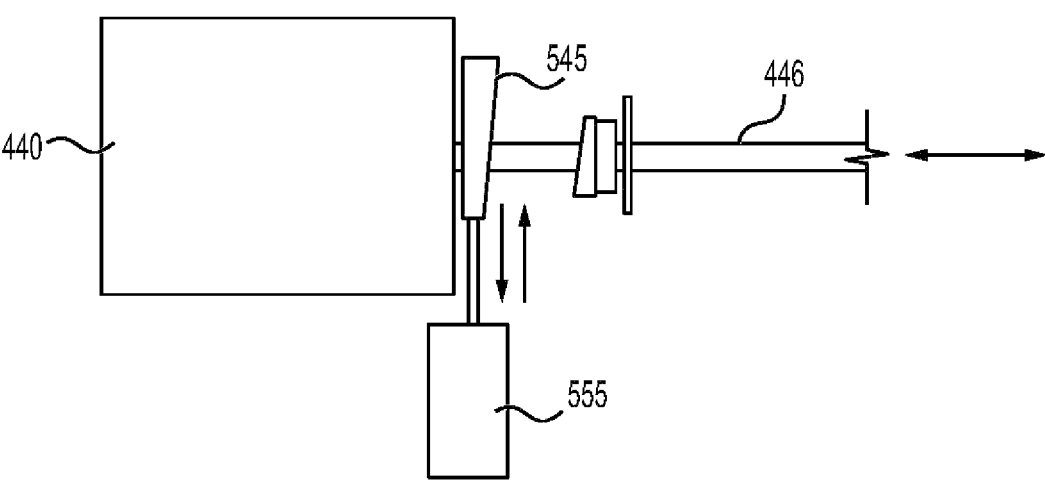
FIG. 5B is a side view of the exemplary positive pressure pulse amplitude adjustment mechanism including an additional opposing taper member to optimize proper alignment of the tapered shim.
Figure 5C:
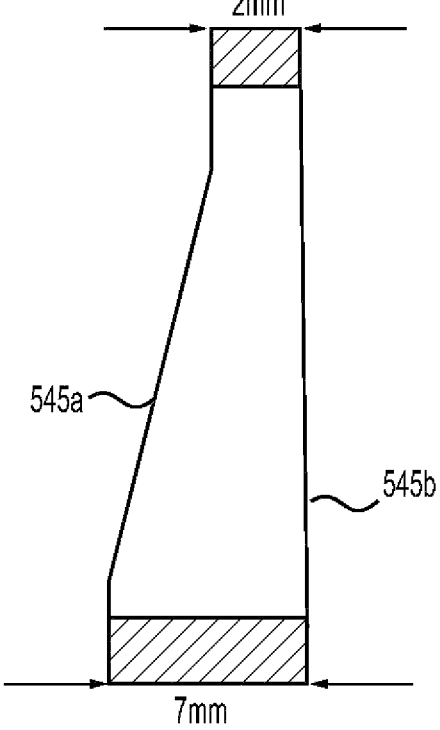
FIG. 5C is an axial cross-sectional view of the tapered shim along lines V(C)-V(C) in FIG. 5A.
Figure 5D:
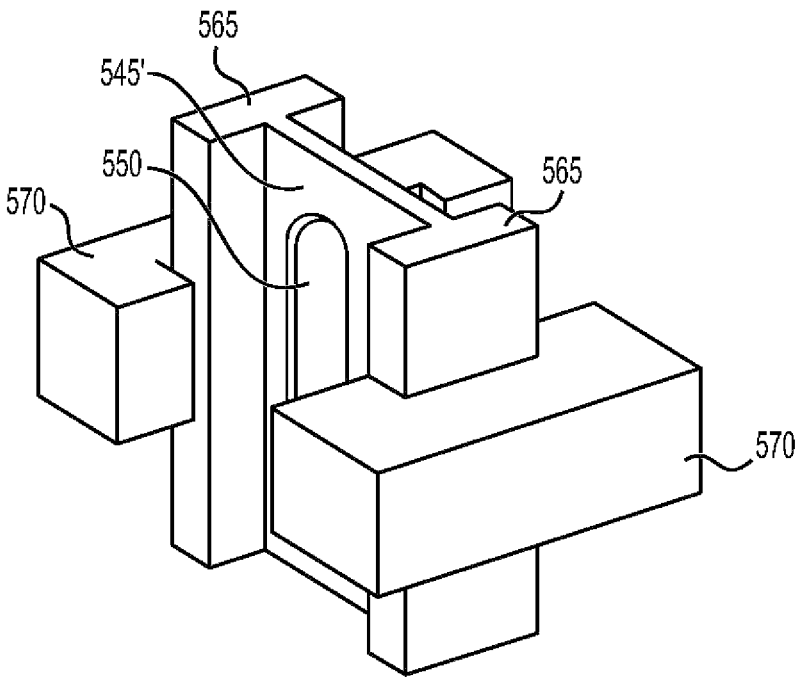
FIG. 5D is a perspective view of the tapered shim of FIG. 5A with an additional feature of guide blocks on opposing lateral sides optimizing proper alignment of the tapered shim.
Figure 5E:
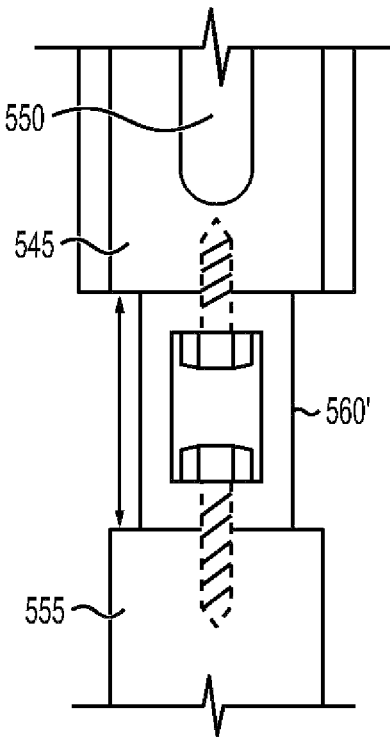
FIG. 5E depicts an alternative non-rigid connection (e.g., rubber connection) between the tapered shim of FIG. 5A and associated supplemental linear actuator.

FIGS. 5A-5C provides an optional mechanism for adjusting the stroke length of the plunger 430 displaced using a solenoid actuator, for example, the cyclic aspiration system in FIGS. 4A-4C. The stroke length adjustment mechanism in FIGS. 5A-5C includes a tapered shim 545 having a slot 550 defined therein through which the shaft 446 extends with the solenoid 440 on a proximal side and the coupling or connection fitting 435' on the distal facing side attachable to the complementary coupling or connection fitting 435 associated with the displaceable plunger (e.g., plunger 430 in FIGS. 4A-4C) of the positive pressure pulse generator mechanism. FIG. 5A is a perspective view assembly of the tapered shim 545 together with the connection fitting 435' and actuator 440, while FIG. 5C is an axial cross-sectional view of the tapered shim 545 alone. The tapered shim 545 has a planar (i.e., flat allowing it to be flush against the actuator 440) proximal facing surface 545b and a distal facing surface 545a tapered at least along a section coinciding with the slot 550. In the example illustrated in FIG. 5C, top and bottom sections of the distal facing surface 545a are not tapered, only the intermediate section therebetween coinciding with the slot 550 is tapered. By way of example, the axial width of the non-tapered top and bottom sections are approximately 2 mm and 7 mm, respectively. The tapered section of the distal facing surface 545a of the tapered shim 545 engages with the coupling or connection fitting 435' limiting the stroke length of the actuator 440. By raising or lowering the tapered shim 545 in a lateral direction perpendicular to the shaft 446, the stroke length of the actuator 440 (as well as the extent of travel of the plunger 430 connected thereto) varies depending on a particular point along the tapered section of the distal facing surface 545a the coupling or connection fitting 435' engages therewith. That is, by lowering the tapered shim 545 relative to the shaft 446 the coupling or connection fitting 435' engages with the narrower upper end of the tapered section of the distal facing surface 545a increasing the stroke length of the actuator 440 and plunger 430 connected thereto thereby increasing in amplitude the generated positive pressure pulse (i.e., higher pressure level). Whereas, by raising the tapered shim 545 relative to the shaft 446 the coupling or connection fitting 435' engages with the wider lower end of the tapered section of the distal facing surface 545a reducing the stroke length of the actuator 440 and plunger 430 connected thereto producing a reduced positive pressure pulse (i.e., lower pressure level). Raising or lowering in the lateral direction the tapered shim 545 to achieve a desired pressure level in the generated positive pressure pulse may be accomplished using its own dedicated supplemental linear displacement device 555 (e.g., linear actuator, solenoid, cam, screw thread, electromagnets, etc.) FIG. 5B is a side view of the arrangement in FIG. 5A and includes an optional additional opposing tapered positioning shim 545' similar to the tapered shim 545 but flipped both axially and laterally relative thereto. Passage through the two shims 545, 545' ensures correct positioning of the shaft 446 while passing therethrough the respective slots. Another optional feature is to provide lateral guide rails on each side of the tapered shim 545 receivable within corresponding tracks of guide blocks 570 to ensure proper alignment of the tapered shim 545 itself. By ensuring proper alignment of the tapered shim 545 as well as the shaft 446 the finer the tuning of amplitude of the generated positive pressure pulse. Connection between the tapered shim 545 and supplemental linear displacement mechanism 555 (e.g., solenoid or linear actuator) may be via a rigid connector (e.g., rigid shaft 560 (FIG. 5A)) or alternatively via a non-rigid (i.e., absorbing) connector (e.g., rubber connector 560' (FIG. 5E)). Rubber connector 560' absorbs or minimizes vibrations of the tapered shim induced during cyclic displacement of the actuator shaft 446 through the slot 550 as well as engagement of the coupling or connection fitting 435' with its distal facing surface 545a. Furthermore, the rubber connector 560' also allows for slight movement back and forth of the tapered shim 545 relative to the supplemental linear displacement mechanism 555 without snapping the connection therebetween.

Figure 6A:
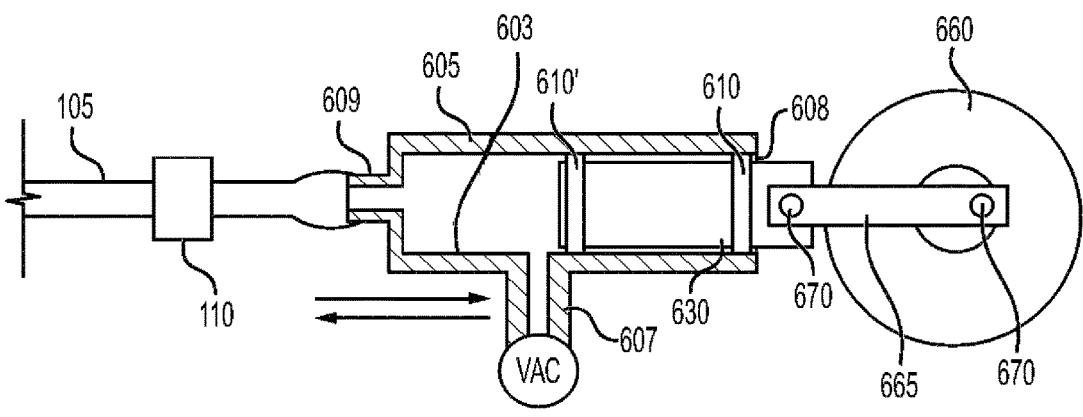
FIG. 6A is another example cyclic aspiration system in accordance with the present disclosure producing the cyclic aspiration pressure waveform using a vacuum pump and a single plunger slidable within a main inner barrel of a rigid housing (e.g., 3-way connector) via an external linear actuator; depicting the single plunger in a retracted state allowing unrestricted passage through a side vacuum pressure inlet port and into the main inner barrel of the rigid housing of the vacuum pressure generated by the vacuum pump; while also depicting (as indicated by the bi-directional arrows) optional adjustment of the return stroke length of the plunger by repositioning (e.g., sliding) the rigid housing relative to the rotating reciprocating motor.
Figure 6B:
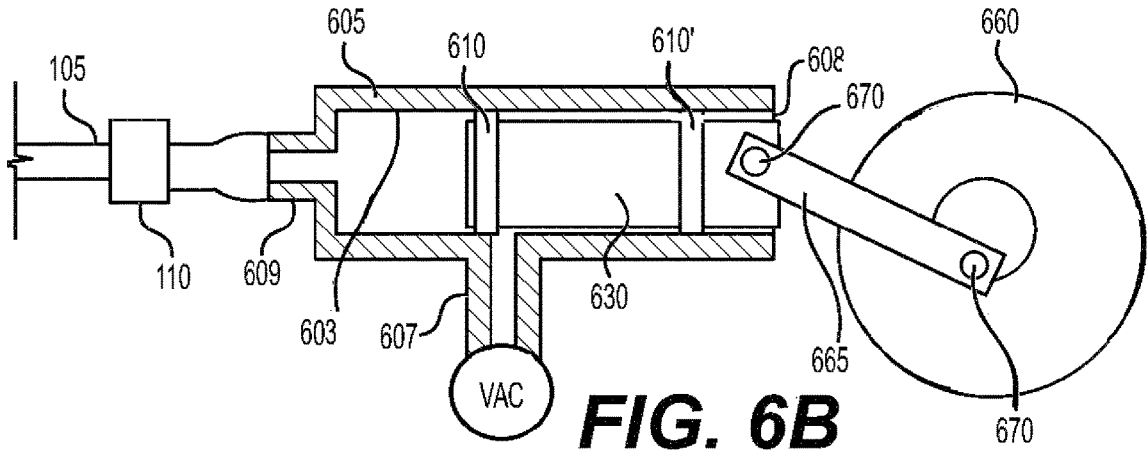
FIG. 6B is the example cyclic aspiration system of FIG. 6A depicting the single plunger in a position partially advanced within the main inner barrel of the rigid housing blocking (i.e., closed state) the side vacuum pressure inlet port of the 3-way connector preventing passage therethrough of the vacuum pressure into the main inner barrel.
Figure 6C:
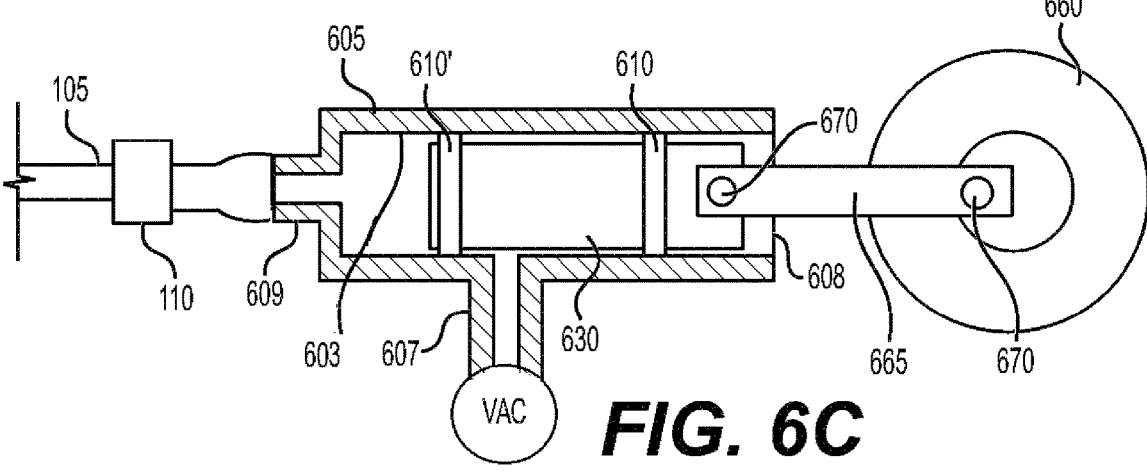
FIG. 6C is the example cyclic aspiration system of FIG. 6A depicting the single plunger in a position fully advanced within the main inner barrel of the rigid housing displacing (i.e., compressing) the fluid collectable therein thereby generating the positive pressure pulse while the side vacuum pressure inlet port remains blocked (i.e., closed state) preventing passage therethrough of the vacuum pressure into the main inner barrel.

FIGS. 6A-6C is still another example in which the positive pressure pulse generator mechanism is a single rotating reciprocating plunger 630 slidable within a main inner barrel 603 defined in a rigid housing 605. In this embodiment the single plunger functions both as a valve (e.g., open/close) allowing or blocking passage therethrough of the vacuum pressure while also compressing fluid collected in the main inner barrel 603 thereby creating the positive pressure pulse. Reciprocating movement is imparted to the plunger 630 using a rotating reciprocating motor. Referring to FIG. 6A, the rigid housing (e.g., 3-way or T-shape connector) 605 includes a proximal inlet port 608 and a distal outlet port 609 with the main inner barrel 603 defined therebetween, while a side port 607 is in fluid communication with the main inner barrel 603. The distal port 609 is connected in fluid communication either directly or indirectly via inlet tubing to the proximal hub 110 of the aspiration catheter 105, while the side port 607 is connected in fluid communication either directly or indirectly via inlet tubing to the vacuum pump 135. Disposed within the main inner barrel 603 of the rigid housing 605 is a single plunger 630 displaceable via a rotating motor 660 secured thereto via a cam shaft 665 and securing pins 670. Plunger 630 includes two seals, i.e., a proximal seal 610 to prevent leakage via the proximal inlet port 608 through which the cam shaft 665 extends and a distal seal 610' to ensure no leakage of the vacuum pressure when the plunger 630 is in a position closing off or blocking the side inlet port 607. FIGS. 6A-6C depict different stages of the plunger 630 as well as the corresponding rotation of the motor 660 cyclically retracting and advancing the plunger 630 within the rigid housing 605 to produce the cyclic aspiration pressure waveform. Referring to FIG. 6A, rotation of the motor 660 retracts the plunger 630 in the proximal direction opening the side inlet port 607 allowing unrestricted passage therethrough of the vacuum pressure into the main inner barrel 603. As the motor 660 continues to rotate, the plunger 630 is partially advanced in a distal direction within the main inner barrel 603 of the rigid housing 605 blocking or closing off the side port 607 prohibiting the vacuum pressure passing into the main inner barrel 603 (FIG. 6B). Continuing rotation of the motor 660 fully advances the plunger 630 within the main inner barrel 603 of the rigid housing 605 compressing the fluid collected therein producing a positive pressure pulse while the side inlet port 607 remains blocked or closed off by the plunger 630 (FIG. 6C). Accordingly, continuous rotation of the motor 660 cyclically retracts, partially advances, and then fully advances the plunger 630 within the main inner barrel

630 of the rigid housing 605 producing the cyclic aspiration pressure waveform of intermittent cyclic intervals of vacuum pressure and positive pressure. This exemplary motor 660 and cam shaft 665 arrangement for linearly displacing the single plunger 630 allows for maximum motor rotation yielding maximum cycling frequency of the plunger 630. In addition, positive pressure generated remains consistent and unchanging since displacement of the plunger 630 is controlled by rotating the motor 660. As indicated in FIG. 6A by the bi-directional arrows, optionally the rigid housing 605 may be slidably mounted on a track repositionable in an axial direction relative to that of the motor 660 to adjust the return stroke length of the plunger 630 thereby varying, controlling or adjusting the positive fluid displacement per cycle (i.e., amplitude of the positive pressure pulse generated).

Aspects of the present disclosure are also provided by the following numbered clauses:

Clause 1

A cyclic aspiration system producing a cyclic aspiration pressure waveform of intermittent cyclic intervals of vacuum pressure below atmospheric pressure and a positive pressure higher than the vacuum pressure, the system comprising: a vacuum pump (135) generating the vacuum pressure; a positive pressure pulse generator mechanism connected in fluid communication with the vacuum pump (135); the positive pressure pulse generator mechanism including at least one displaceable member (130, 230a, 230b, 320, 325, 430, 630) displaceable within a housing (140, 305, 405, 605), wherein the at least one displaceable member controls passage therethrough the housing of the vacuum pressure and produces the positive pressure pulse by compressing collectable fluid therein; an aspiration catheter (105) connected in fluid communication with the positive pressure pulse generator mechanism; and at least one actuator (125, 125', 225a, 225b, 225c, 227, 340, 440, 660, 665) arranged externally of the housing displacing the at least one displaceable member (130, 230a, 230b, 320, 325, 430, 630) within the housing (140, 140', 305, 405, 605).

Clause 2

The cyclic aspiration system of Clause 1, wherein the at least one displaceable member (130, 230a, 230b, 320, 325, 430, 630) is a single displaceable member.

Clause 3

The cyclic aspiration system of Clause 1, wherein the at least one displaceable member includes a first displaceable member (230a, 325) and a second displaceable member (230b, 320), each independently displaceable in the housing (305); wherein the first displaceable member (230a, 325) is configured to control passage therethrough the housing of the vacuum pressure and the second displaceable member (230b, 320) is configured to produce the positive pressure pulse by compressing the collectable fluid therein.

Clause 4

The cyclic aspiration system of any of Clauses 1 through 3, wherein the at least one displaceable member is at least one electrically conductive plunger (130, 230a, 230b) displaceable within a channel (115c) defined in the housing (140, 140'); and the actuator is a plurality of electromagnets (125, 125', 225a, 225b, 225c, 227) arranged externally of the housing (140, 140').

Clause 5

The cyclic aspiration system of Clause 1, wherein the at least one displaceable member is a flexible diaphragm (320) and ball valve (325) secured thereto projecting into an internal cavity of the housing (305).

Clause 6

The non-vented cyclic aspiration system of any of Clauses 1 through 2, wherein the housing (405, 605) has a main inner barrel (403, 603) defined therein and a side vacuum inlet port (407, 607) in fluid communication with the main inner barrel (403, 603); and the at least one displaceable member is a single plunger (430, 630) displaceable in the main inner barrel (403, 603) of the housing (405, 605).

Clause 7

The cyclic aspiration system of any of Clauses 1 through 6, further comprising a positive pressure pulse amplitude adjustment mechanism varying a maximum return travel of the at least one displaceable member within the housing.

Clause 8

The cyclic aspiration system of any of Clauses 1 through 7, wherein the at least one actuator is a plurality of electro-magnets, a linear actuator, a solenoid, a reciprocating motor, or a rotating reciprocating motor.

Clause 9

The cyclic aspiration system of any of Clauses 1 through 8, wherein the positive pressure pulse generator mechanism is contaminable by blood and discardable after a single use; while the at least one actuator (125, 125', 225a, 225b, 225c, 227, 340, 440, 660, 665) is separable from the positive pressure pulse generator, not contaminable by blood, and reusable.

Clause 10

A method of using a cyclic aspiration system to produce a cyclic aspiration pressure waveform of intermittent cyclic intervals of vacuum pressure below atmospheric pressure and a positive pressure higher than the vacuum pressure; wherein the cyclic aspiration system includes: a vacuum pump (135) generating the vacuum pressure; a positive pressure pulse generator mechanism connected in fluid communication with the vacuum pump (135); the positive pressure pulse generator mechanism including at least one displaceable member (130, 230a, 230b, 320, 325, 430, 630) displaceable within a housing (140, 140', 305, 405, 605), wherein the at least one displaceable member (130, 230a, 230b, 320, 325, 430, 630) controls passage therethrough the housing (140, 140', 305, 405, 605) of the vacuum pressure and produces the positive pressure pulse by compressing collectable fluid therein; an aspiration catheter (105) connected in fluid communication with the positive pressure pulse generator mechanism; and at least one actuator (125, 125', 225a, 225b, 225c, 227, 340, 440, 660, 665) arranged externally of the housing (140, 140', 305, 405, 605) displacing the at least one displaceable member (130, 230a, 230b, 320, 325, 430, 630) within the housing (140, 140', 305, 405, 605); wherein the method comprises the steps of: delivering the aspiration catheter (105) through a vessel to a target site on a proximal side of a clot; applying the vacuum pressure generated by the vacuum pump (135); and producing the cyclic aspiration pressure waveform by moving the at least one displaceable member (130, 230a, 230b, 320, 325, 430, 630) via the at least one actuator (125, 125', 225a, 225b, 225c, 227, 340, 440, 660, 665) to control passage therethrough the housing (140, 140', 305, 405, 605) of the vacuum pressure while also intermittently cyclically producing the positive pressure pulse by compressing collectable fluid therein.

Clause 11

The method of Clause 10, wherein the step of producing the cyclic aspiration pressure waveform comprises during the vacuum pressure interval allowing passage therethrough the housing (140, 140', 305, 405, 605) of the vacuum pressure generated by the vacuum pump (135); and during the positive pressure interval prohibiting passage therethrough the housing (140, 140', 305, 405, 605) of the vacuum pressure generated by the vacuum pump.

Clause 12

The method of Clause 11, wherein the step of producing the cyclic aspiration pressure waveform further comprises during the positive pressure interval compressing the collectable fluid in the housing (140, 140', 305, 405, 605) to create the positive pressure pulse.

Clause 13

The method of any of Clauses 10 through 12, wherein the at least one displaceable member (130, 230a, 230b, 320, 325, 430, 630) is a single displaceable member.

Clause 14

The method of any of Clauses 10 through 12, wherein the at least one displaceable member includes a first displaceable member (230a, 325) and a second displaceable member (230b, 320), each independently displaceable in the housing (305); wherein the first displaceable member (230a, 325) is configured to control passage therethrough the housing of the vacuum pressure and the second displaceable member (230b, 320) is configured to produce the positive pressure pulse by compressing the collectable fluid therein.

Clause 15

The method of Clause 10 through 14, wherein the at least one displaceable member is at least one electrically conductive plunger (130, 230a, 230b) displaceable within a channel (115c) defined in the housing (140, 140'); and the actuator is a plurality of electromagnets (125, 125', 225a, 225b, 225c, 227) arranged externally of the housing (140, 140').

Clause 16

The method of Clause 10 in accordance with claim 10, wherein the at least one displaceable member is a flexible diaphragm (320) and ball valve (325) secured thereto projecting into an internal cavity of the housing (305).

Clause 17

The method of any of Clauses 10 through 13, wherein the housing (405, 605) has a main inner barrel (403, 603) defined therein and a side vacuum inlet port (407, 607) in fluid communication with the main inner barrel (403, 603); and the at least one displaceable member is a single plunger (430, 630) displaceable in the main inner barrel (403, 603) of the housing (405, 605).

Clause 18

The method of any of Clauses 10 through 17, further comprising a positive pressure pulse amplitude adjustment mechanism varying a maximum return travel of the at least one displaceable member within the housing.

Clause 19

The method of any of Clauses 10 through 18, wherein the positive pressure pulse generator mechanism is contaminable by blood and discardable after a single use; while the at least one actuator (125, 125', 225a, 225b, 225c, 227, 340, 440, 660, 665) is separable from the positive pressure pulse generator, not contaminable by blood, and reusable.

Clause 20

The method of any of Clauses 10 through 19, wherein the at least one displaceable member is a plunger.

The descriptions contained herein are examples and are not intended in any way to limit the scope of the present disclosure. As described herein, the present disclosure contemplates many variations and modifications of the cyclic aspiration system producing the cyclic aspiration waveform using a positive pressure pulse generator mechanism associated with a housing disposed in fluid communication between a vacuum pump and aspiration catheter, wherein the positive pressure pulse generator mechanism using at least one displaceable member displaceable within the housing via at least one actuator arranged externally thereof controls (i.e., allowing or prohibiting) passage of the vacuum pressure therethrough and creates the positive pressure pulse by compressing fluid collectable therein. Modifications and variations apparent to those having skilled in the pertinent art according to the teachings of this disclosure are intended to be within the scope of the claims which follow.

What is claimed is:

1. A cyclic aspiration system producing a cyclic aspiration pressure waveform of intermittent cyclic intervals of vacuum pressure below atmospheric pressure and a positive pressure higher than the vacuum pressure, the system comprising:

a vacuum pump generating the vacuum pressure;

a positive pressure pulse generator mechanism connected in fluid communication with the vacuum pump; the positive pressure pulse generator mechanism including at least one displaceable member displaceable within a housing, wherein the at least one displaceable member controls passage therethrough the housing of the vacuum pressure and produces the positive pressure pulse by compressing collectable fluid therein;

an aspiration catheter connected in fluid communication with the positive pressure pulse generator mechanism; and at least one actuator arranged externally of the housing displacing the at least one displaceable member within the housing;

wherein the at least one displaceable member includes a first displaceable member and a second displaceable member, each independently displaceable in the housing; wherein the first displaceable member is configured to control passage therethrough the housing of the vacuum pressure and the second displaceable member is configured to produce the positive pressure pulse by compressing the collectable fluid therein.

2. The cyclic aspiration system in accordance with claim 1, wherein the at least one displaceable member is at least one electrically conductive plunger displaceable within a channel defined in the housing; and the actuator is a plurality of electromagnets arranged externally of the housing.

3. The cyclic aspiration system in accordance with claim 1, wherein the at least one actuator is a plurality of electromagnets, a linear actuator, a solenoid, a reciprocating motor, or a rotating reciprocating motor.

4. The cyclic aspiration system in accordance with claim 1, wherein the positive pressure pulse generator mechanism is contaminable by blood and discardable after a single use; while the at least one actuator is separable from the positive pressure pulse generator, not contaminable by blood, and reusable.

5. A method of using a cyclic aspiration system to produce a cyclic aspiration pressure waveform of intermittent cyclic intervals of vacuum pressure below atmospheric pressure and a positive pressure higher than the vacuum pressure; wherein the cyclic aspiration system includes: a vacuum pump generating the vacuum pressure; a positive pressure pulse generator mechanism connected in fluid communication with the vacuum pump; the positive pressure pulse generator mechanism including at least one displaceable member displaceable within a housing, wherein the at least one displaceable member controls passage therethrough the housing of the vacuum pressure and produces the positive pressure pulse by compressing collectable fluid therein; an aspiration catheter connected in fluid communication with the positive pressure pulse generator mechanism; and at least one actuator arranged externally of the housing displacing the at least one displaceable member within the housing; wherein the method comprises:

delivering the aspiration catheter through a vessel to a target site on a proximal side of a clot;

applying the vacuum pressure generated by the vacuum pump; and producing the cyclic aspiration pressure waveform by moving the at least one displaceable member via the at least one actuator to control passage therethrough the housing of the vacuum pressure while also intermittently cyclically producing the positive pressure pulse by compressing collectable fluid therein;

wherein the at least one displaceable member includes a first displaceable member and a second displaceable member, each independently displaceable in the housing; wherein the first displaceable member is configured to control passage therethrough the housing of the vacuum pressure and the second displaceable member is configured to produce the positive pressure pulse by compressing the collectable fluid therein.

6. The method in accordance with claim 5, wherein the producing the cyclic aspiration pressure waveform comprises during the vacuum pressure interval allowing passage therethrough the housing of the vacuum pressure generated by the vacuum pump; and during the positive pressure interval prohibiting passage therethrough the housing of the vacuum pressure generated by the vacuum pump.

7. The method in accordance with claim 6, wherein the producing the cyclic aspiration pressure waveform further comprises during the positive pressure interval compressing the collectable fluid in the housing to create the positive pressure pulse.

8. The method in accordance with claim 5, wherein the at least one displaceable member is at least one electrically conductive plunger displaceable within a channel defined in the housing; and the actuator is a plurality of electromagnets arranged externally of the housing.

9. The method in accordance with claim 5, wherein the positive pressure pulse generator mechanism is contaminable by blood and discardable after a single use; while the at least one actuator is separable from the positive pressure pulse generator, not contaminable by blood, and reusable.

10. The method in accordance with claim 5, wherein the at least one displaceable member is a plunger.

11. A cyclic aspiration system producing a cyclic aspiration pressure waveform of intermittent cyclic intervals of vacuum pressure below atmospheric pressure and a positive pressure higher than the vacuum pressure, the system comprising:

a vacuum pump generating the vacuum pressure;

a positive pressure pulse generator mechanism connected in fluid communication with the vacuum pump; the positive pressure pulse generator mechanism including at least one displaceable member displaceable within a housing, wherein the at least one displaceable member controls passage therethrough the housing of the vacuum pressure and produces the positive pressure pulse by compressing collectable fluid therein;

an aspiration catheter connected in fluid communication with the positive pressure pulse generator mechanism; and at least one actuator arranged externally of the housing displacing the at least one displaceable member within the housing;

wherein the at least one displaceable member is a flexible diaphragm and ball valve secured thereto projecting into an internal cavity of the housing.

12. A cyclic aspiration system producing a cyclic aspiration pressure waveform of intermittent cyclic intervals of vacuum pressure below atmospheric pressure and a positive pressure higher than the vacuum pressure, the system comprising:

a vacuum pump generating the vacuum pressure;

a positive pressure pulse generator mechanism connected in fluid communication with the vacuum pump; the positive pressure pulse generator mechanism including at least one displaceable member displaceable within a housing, wherein the at least one displaceable member controls passage therethrough the housing of the vacuum pressure and produces the positive pressure pulse by compressing collectable fluid therein;

an aspiration catheter connected in fluid communication with the positive pressure pulse generator mechanism;

at least one actuator arranged externally of the housing displacing the at least one displaceable member within the housing; and a positive pressure pulse amplitude adjustment mechanism varying a maximum return travel of the at least one displaceable member within the housing.

13. A method of using a cyclic aspiration system to produce a cyclic aspiration pressure waveform of intermittent cyclic intervals of vacuum pressure below atmospheric pressure and a positive pressure higher than the vacuum pressure; wherein the cyclic aspiration system includes: a vacuum pump generating the vacuum pressure; a positive pressure pulse generator mechanism connected in fluid communication with the vacuum pump; the positive pressure pulse generator mechanism including at least one displaceable member displaceable within a housing, wherein the at least one displaceable member controls passage therethrough the housing of the vacuum pressure and produces the positive pressure pulse by compressing collectable fluid therein;

an aspiration catheter connected in fluid communication with the positive pressure pulse generator mechanism; and at least one actuator arranged externally of the housing displacing the at least one displaceable member within the housing; wherein the at least one displaceable member is a flexible diaphragm and ball valve secured thereto projecting into an internal cavity of the housing; wherein the method comprises:

delivering the aspiration catheter through a vessel to a target site on a proximal side of a clot;

applying the vacuum pressure generated by the vacuum pump; and producing the cyclic aspiration pressure waveform by moving the at least one displaceable member via the at least one actuator to control passage therethrough the housing of the vacuum pressure while also intermittently cyclically producing the positive pressure pulse by compressing collectable fluid therein.

14. A method of using a cyclic aspiration system to produce a cyclic aspiration pressure waveform of intermittent cyclic intervals of vacuum pressure below atmospheric pressure and a positive pressure higher than the vacuum pressure; wherein the cyclic aspiration system includes: a vacuum pump generating the vacuum pressure; a positive pressure pulse generator mechanism connected in fluid communication with the vacuum pump; the positive pressure pulse generator mechanism including at least one displaceable member displaceable within a housing, wherein the at least one displaceable member controls passage therethrough the housing of the vacuum pressure and produces the positive pressure pulse by compressing collectable fluid therein;

an aspiration catheter connected in fluid communication with the positive pressure pulse generator mechanism; at least one actuator arranged externally of the housing displacing the at least one displaceable member within the housing; and a positive pressure pulse amplitude adjustment mechanism varying a maximum return travel of the at least one displaceable member within the housing; wherein the method comprises:

delivering the aspiration catheter through a vessel to a target site on a proximal side of a clot;

applying the vacuum pressure generated by the vacuum pump; and producing the cyclic aspiration pressure waveform by moving the at least one displaceable member via the at least one actuator to control passage therethrough the housing of the vacuum pressure while also intermittently cyclically producing the positive pressure pulse by compressing collectable fluid therein.

\* \* \* \* \*